(12) United States Patent
Takeuchi et al.

(10) Patent No.: US 6,214,340 B1
(45) Date of Patent: Apr. 10, 2001

(54) PHYSIOLOGICALLY ACTIVE SUBSTANCE SULPHOSTIN, PROCESS FOR PRODUCING THE SAME, AND USE THEREOF

(75) Inventors: Tomio Takeuchi; Masa Hamada; Yasuhiko Muraoka; Tetsuo Akiyama; Masatoshi Abe; Hiroshi Naganawa; Yoshikazu Takahashi, all of Tokyo (JP)

(73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 09/554,362

(22) PCT Filed: Nov. 17, 1998

(86) PCT No.: PCT/JP98/05164

§ 371 Date: May 12, 2000

§ 102(e) Date: May 12, 2000

(87) PCT Pub. No.: WO99/25719

PCT Pub. Date: May 27, 1999

(30) Foreign Application Priority Data

Nov. 18, 1997 (JP) .................................................... 9-317221

(51) Int. Cl.$^7$ ................................ C12N 1/20; C12N 9/99; A61K 35/74; C07G 17/00; C12P 1/06
(52) U.S. Cl. .................... 424/117; 435/252.1; 514/18; 530/321
(58) Field of Search ............................... 514/18; 530/321; 435/252.1; 424/117, 123

(56) References Cited

FOREIGN PATENT DOCUMENTS

| WO 94/03055 | 2/1994 | (WO) . |
| WO 95/11689 | 5/1995 | (WO) . |
| WO 95/29691 | 11/1995 | (WO) . |
| WO 97/40832 | 11/1997 | (WO) . |

OTHER PUBLICATIONS

Immunol. Today, 15, pp. 180–184 (1994) "CD26: a surface protease involved in T–cell activation"; Bernhard Fleischer.

J. Clin. Invest., 83, pp. 1533–1540 (1989); "Dipeptidylpeptidase IV and Trypsin–like Enzymatic Degradation . . . "; Lawrence A. Frohman, et al.

J. of Antibiotics, 37, pp. 422–425 (1984); "Diprotins A and B, Inhibitors of Dipeptidyl, Aminopeptidase IV, produced by Bacteria".

Patent Abstracts of Japan vol. 1996, No. 11, Nov. 29, 1996.

*Primary Examiner*—Herbert J. Lilling
(74) *Attorney, Agent, or Firm*—Nields & Lemack

(57) ABSTRACT

This invention provides a physiologically active substance having a strong dipeptidyl peptidase IV inhibitory activity. The physiologically active substance sulphostin is obtained by culturing a microorganism belonging to the genus Streptomyces and having an ability to produce the physiologically active substance sulphostin, producing and accumulating this substance in the cultures, and harvesting it from the cultures.

6 Claims, 4 Drawing Sheets

PHYSIOLOGICALLY ACTIVE SUBSTANCE SULPHOSTIN, PROCESS FOR PRODUCING THE SAME, AND USE THEREOF

The present invention relates to a novel physiologically active substance sulphostin, a process for producing the same and use thereof. The compound of this invention has a dipeptidylpeptidase IV inhibitory activity. Dipeptidylpeptidase IV which occurs on the surface of T cells is known to take part in activation of T cells (Immunol. Today, 15, 180–184 (1994)), and it plays an important role in the immune system. Dipeptidylpeptidase IV is also associated with degradation of a growth hormone-releasing hormone in serum (J. Clin. Invest., 83, 1533–1540 (1989)). The compound of the present invention, therefore, is expected to find its use as a physiologically active substance for various medicinal and pharmaceutical preparations such as immune regulators, hormone regulators, anti-HIV drugs, antiallergic drugs, antiphlogistics, antirheumatics, etc.

BACKGROUND ART

Some compounds such as Diprotin A and B (J. of Antibiotics, 37, 422–425 (1984)) have been known as physiologically active substances having the dipeptidylpeptidase IV inhibitory activity.

These compounds, however, are weak in their inhibitory activity against the above enzyme and are unsatisfactory for use as a physiologically active substance in the above medicinal and pharmaceutical preparations. Therefore, the advent of a novel compound which is suited for such uses has been waited.

DISCLOSURE OF THE INVENTION

In view of the above, the present inventors have pursued extensive research on the microbial metabolites, and as a result found that a strain belonging to the actinomycetes is capable of producing a physiologically active substance sulphostin having an excellent dipeptidylpeptidase IV inhibitory activity. The present invention has been attained on the basis of this finding.

The physiologically active substance sulphostin of the present invention can be obtained by culturing a sulphostin producing microorganism belonging to the genus Streptomyces, allowing the microorganism to produce and accumulate the physiologically active substance in the culture medium, and harvesting the substance from the culture medium.

BEST MODE FOR CARRYING OUT THE INVENTION

Figure 1:
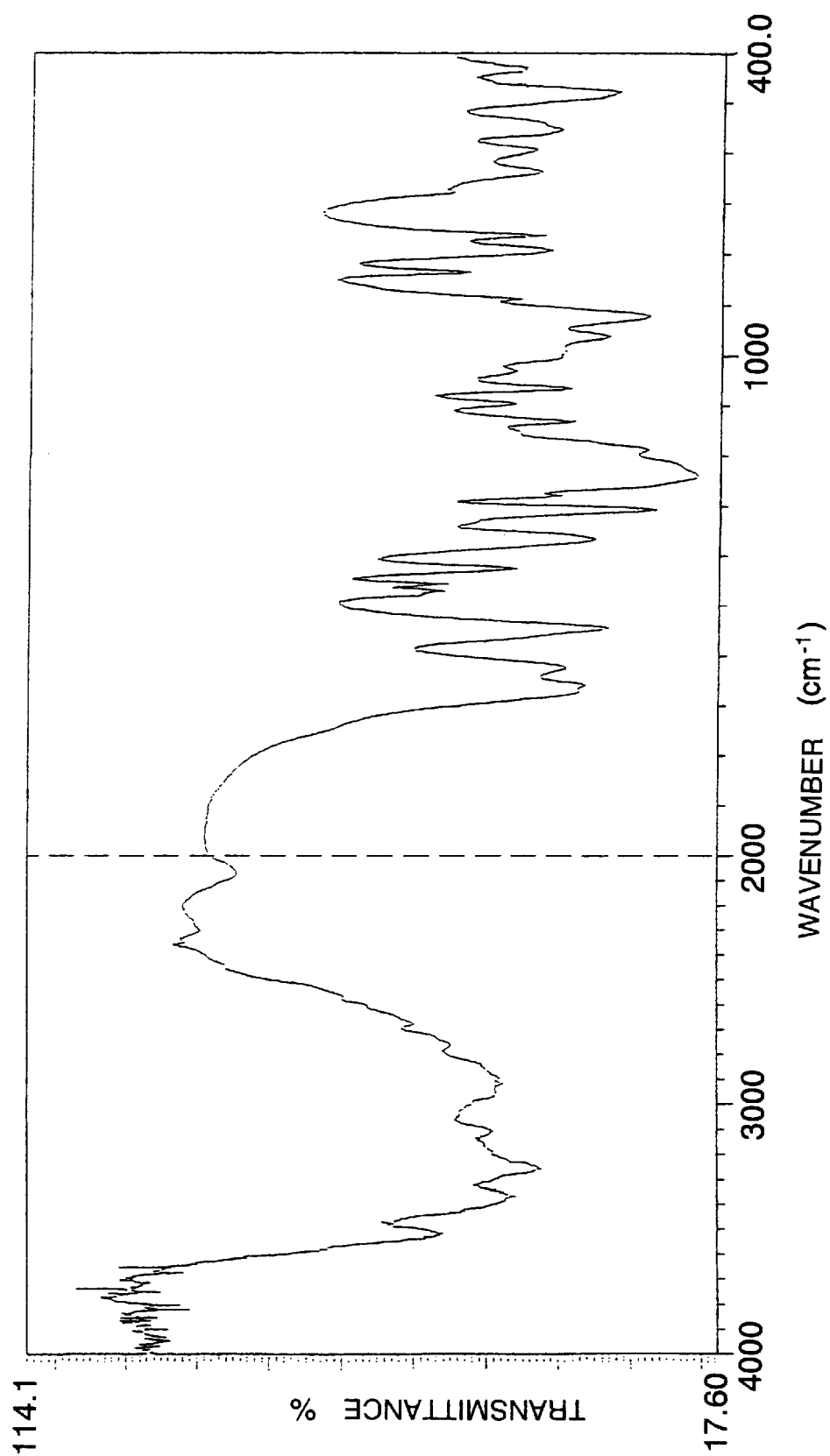
FIG. 1 is an infrared absorption spectrum of sulphostin measured with a potassium bromide tablet.

A typical example of the sulphostin-producing microorganisms is Streptomyces sp. MK251-43F3 strain which was isolated from the soil at Hamo-machi, Sado-gun, Niigata-ken by Microbial Chemical Research Institute in September 1994 (This strain was deposited in and accepted by National Institute of Bioscience and Human-Technology of the Agency of Industrial Science and Technology, at 1-3, Higashi-1-chome, Tsukuba-shi, Ibaraki-ken, 305-8566, Japan on Feb. 6, 1997 under FERM BP-6571). This strain is an example of those strains which can be used most effectively in the present invention. The mycrological and physiological properties of this strain are as described below.

1. Morphological Properties

MK251-43F3 strain elongates the helix-forming aerial hyphae from the branched substrate hyphae. A matured spore link has 10 to 50 or more oval spores, and the size of one spore is about 0.6–0.8 $\mu$m×about 0.8–0.9 $\mu$m. The spore surface is spiny or capillary. There are no verticillate hyphae and rhizomorph in the mycelium. Nor are present the sporangia and motile spores.

2. Growth in Various Types of Medium

Regarding the color of the colonies on the medium, the color expression according to the Color Harmony Manual of Container Corporation of America was given in brackets as a standard of color after the common color name.

(1) Sucrose-nitrate agar medium (cultured at 27° C.)

White to brownish white (3ba, Pearl) aerial hyphae adhere thinly to colorless grown colonies. No soluble pigment is found.

(2) Glycerin-asparagine agar medium (ISP medium 5, cultured at 27° C.)

The growth is light yellow (2cd, Ivory Tint). No adhesion of aerial hyphae takes place. No soluble pigment is admitted.

(3) Starch-inorganic salt agar medium (ISP medium 4, cultured at 27° C.)

White to brownish white aerial hyphae adhere slightly on the colorless to light yellowish brown (2gc, Bamboo) growth. No soluble pigment is admitted.

(4) Tyrosine agar medium (ISP medium 7, cultured at 27° C.)

The growth is colorless to light yellow (2cb, Ivory Tint). Adhesion of aerial hyphae is bad. After 3 weeks of culture, scanty white aerial hyphae adhere only partially. No soluble pigment is admitted.

(5) Yeast-malt aerial medium (ISP medium 2, cultured at 27° C.)

White aerial hyphae adhere slightly on the colorless to light yellow (2gc, Bamboo) growth. No soluble pigment is admitted.

(6) Oatmeal agar medium (ISP medium 3, cultured at 27° C.)

Light pink (5ec, Dusty Peach) aerial hyphae adhere on the colorless to light yellow (2ca, Lt Ivory) growth. No soluble pigment is admitted.

3. Physiological Properties (1) Temperature range suited for growth

As a result of the tests conducted at 10° C., 20° C., 24° C., 27° C., 30° C., 37° C. and 50° C. using an yeast-starch agar medium (1% soluble starch, 0.2% yeast extract and 2.4% fibrous agar, pH 7.0), it was found that the cultures grew at any of the tested temperatures except for 10° C. and 50° C. The optimal temperature for the growth appears to be around 30° C.

(2) Hydrolysis of starch (starch-inorganic salt agar medium, ISP medium 4, cultured at 27° C.)

Hydrolysis of starch became perceptible from around the 5th day after start of culture. The hydrolytic action was of a medium degree.

(3) Growth of melanin-like pigment (tryptone-yeast broth (ISP medium 1), peptone-yeast-iron agar medium (ISP medium 6) and tyrosine agar medium (ISP medium 7), cultured at 27° C. in each case)

Negative in each medium.

(4) Utilization of carbon source Pridham-Gottlieb agar medium (ISP medium 9, cultured at 27° C.)

D-glucose, L-arabinose, D-xylose, rhamnose and raffinose are utilized for the growth. Inositol is probably utilized. D-fructose, sucrose and D-mannitol are not utilized.

(5) Nitrate reduction (peptone solution containing 0.1% of potassium nitrate (ISP medium 8), cultured at 27° C.)

This reduction reaction is negative.

(6) Liquefaction of gelatin (15% simple gelatin medium, cultured at 20° C.; glucose-peptone-gelatin medium, cultured at 27° C.)

In the case of the 15% simple gelatin medium, growth at 20° C. was bad and there was the necessity for a retest, but liquefaction of gelatin was not observed. In the case of the glucose-peptone-gelatin medium, liquefaction of gelatin began to take place from around the 18th day after start of culture, but its action was very weak. In this case, too, however, there is the necessity for a retest.

(7) Coagulation and peptonization of skim milk (skim milk powder, cultured at 37° C.)

Peptonization begins without congulation from around the 10th day after start of culture. Its action is weak to medium.

To sum up the above description of properties, the MK251-43F3 strain elongates the helix-forming aerial hyphae from the branched substrate hyphae and each of its matured spore links has 10 to 50 oval-shaped spores. Its surface configuration is spiny or capillary. The growth is colorless or assumes light yellow in various media. Although the aerial hyphae may not adhere in some cases, the growth presents white to brownish white to light pink color in a few media. No soluble pigment is produced. The optimal temperature for the growth is around 30° C. Growth of the melanin-like pigment is negative, and starch hydrolyzability is of a medium degree. Proteolytic ability is low to medium, though there is the necessity for a retest. The 2,6-diaminopimelic acid contained in the cell wall was LL type. The mycelial component menaquinone primarily contains MK-9 (H6) and also contains MK-9 (H8).

In view of these properties, the MK251-43F4 strain is considered to belong to the genus Streptomyces. The analogous strains which have already been isolated include: *Streptomyces flaveolus* (literature: International Journal of Systematic Bacteriology, Vol. 18, page 112 (1968)) and *Streptomyces fasiculatus* (literature: International Journal of Systematic Bacteriology, Vol. 18, page 108 (1968)). The above-mentioned two conserved strains and the MK251-43F3 strain are now under comparative study, but at this point, the MK251-43F3 strain is called Streptomyces sp. MK251-43F3.

The MK251-43F3 strain was deposited at National Institute of Bioscience and Human-Technology of the Agency of Industrial Science and Technology, 1-3, Higashi-1-chome, Tsukuba-shi, Ibaraki-ken, accepted as FERM P-16065 on 6 February 1997, and transferred to the international depositary authority as FERM BP-6571 according to the Budapest Treaty on the International Recognition of the Deposit of Micro-organisms for the Purpose of Patent Procedure on Nov. 11, 1998. All restrictions imposed by the depositor on the availability to the public of the deposited material will be irrevocably removed upon the granting of a patent.

The strain belonging to the genus Streptomyces used in the present invention is liable to change in its properties like other Streptomyces strains. For example, it is easily mutated by the artificial mutating means such as exposure to UV rays or X-ray or application of a chemical substance, but all the mutants can be used in the present invention as far as they have an ability to produce the physiological active substance sulphostin of the present invention.

For producing sulphostin, first the said strain is cultured aerobically in a medium containing the nutrients which are suited for growing the actinomycetes. As the nutrients, it is possible to use the known ones which have commonly been utilized for the culture of the actinomycetes. For instance, as carbon source, glucose, fructose, glycerin, sucrose, dextrin, galactose, organic acids, etc., can be used either singly or in admixture.

As the inorganic and organic nitrogen sources, ammonium chloride, ammonium sulfate, urea, ammonium nitrate, sodium nitrate, peptone, meat extract, yeast extract, dry yeast, corn steep liquor, soybean flour, cottonseed oil cake, Casamino acid, bactosoytone, soluble vegetable proteins, oatmeal and the like can be used either singly or in admixture.

Where necessary, inorganic salts such as sodium chloride, calcium carbonate, magnesium sulfate, copper sulfate, iron sulfate, zinc sulfate, manganese chloride, phosphates, etc., can be added to the medium. It is also possible to properly add organic substances such as amino acids, vitamins, nuclear acids, etc., and/or inorganic substances to the medium.

For cultivation, liquid culture, especially deep spinner culture is best suited in the present invention. It is preferred to carry out culture at a slightly acidic to slightly alkaline pH at 20 to 45° C.

In the case of liquid culture, sulphostin is produced and accumulated in the medium in usually 3 to 8 days of culture. When the production of sulphostin in the cultures reaches the maximum, the cultivation is stopped, then the cells and the culture medium are separated by filtration, and the objective substance is isolated from the cells and purified. For isolating and purifying the objective substance from the cells, the known separation and purification methods commonly utilized for isolating the microbial metabolates from the cells in the culture can be used.

For example, the medium (15 liters) used therefor is separated into the filtrate and the cells by an ordinary filtration method. The obtained filtrate is deaerated and stirred for 2 hours with activated carbon which has been equilibrated with water, and the mixture is subjected to an ordinary filtration method to obtain the activated carbon non-adsorbed fraction. This fraction is concentrated under reduced pressure, suspended in 10 equivalents of ethanol and filtered to give an ethanol insoluble fraction. This ethanol insoluble fraction is further washed with methanol and evaporated to dryness under reduced pressure to obtain a methanol insoluble fraction.

The methanol insoluble fraction is subjected to microcrystalline cellulose column chromatography (Funacel mfd. by Funakoshi Ltd.) with a developing solvent of n-butanol, acetic acid and water (2:1:1) to obtain an active fraction. This active fraction is evaporated to dryness under reduced pressure, lyophilized and then subjected to microcrystalline cellulose column chromatography with a developing solvent of n-butanol, acetic acid and water (3:1:1) to obtain an active fraction. This active fraction is evaporated to dryness under reduced pressure and lyophilized to obtain a crude material. This crude material is dissolved in a 0.2N ammonium bicarbonate solution and subjected to DEAE Sephadex A-25 column chromatography (Pharmacia) developed with a 0.2N ammonium bicarbonate solution to obtain an active fraction. This active fraction is evaporated to dryness under reduced pressure, lyophilized, dissolved in a 0.03N ammonium bicarbonate solution and subjected to a high-performance liquid chromatography (Pharmacia) using SHODEX IEC DEAE-825 columns, which is developed with a 0.03N ammonium bicarbonate solution, to obtain sulphostin (0.5 mg).

The physicochemical properties of the thus obtained physiologically active substance sulphostin are shown below.
1) Appearance: white powder
2) Molecular weight: 272
3) Molecular formula: $C_5H_{13}N_4O_5SP$
4) Solubility: soluble in water and insoluble in lower alcohol, acetone, ethyl acetate, hexane and petroleum ether.
5) Rf value measured by silica gel thin-layer chromatography: 0.28 with a developing solvent of n-butanol, acetic acid and water (2:1:1).
6) Ultraviolet absorption spectrum: A terminal absorption is shown.
7) Infrared absorption spectrum: Shown in FIG. 1 (measured in a potassium bromide tablet). The following specific absorption bands ($cm^{-1}$) are shown: 3510, 3355, 3250, 1672, 1658, 1624, 1545, 1365, 1308, 1240, 1188, 1130, 1064 and 922.
8) Proton NMR spectrum: Shown in FIG. 2 (measured in heavy water). The following signals δ (ppm) are shown: 4.18 (1H, dd, J=6.8, 12.0 Hz), 3.82 (1H, tdd, J=5.1, 7.3, 13.0 Hz), 3.70 (1H, tdd, J=5.1, 6.7, 13.0 Hz), 2.39–2.44 (1H, m), 2.10–2.28 (1H, m), and 1.89–2.03 (2H, m).
9) Carbon 13 NMR spectrum: Shown in FIG. 3 (measured in heavy water): The following signals δ (ppm) are shown: 20.5, 24.2, 45.4, 51.3 and 172.4.
10) Phosphorus NMR spectrum: Shown in FIG. 4 (measured in heavy water). The following signal δ (ppm) is shown: 6.01 11) Specific rotation: $[\alpha]_D^{28}$ –21.5° (c: 0.52; $H_2O$)
12) Melting point: 203–208° C. (decomposed)
13) Color reaction: positive to ninhydrin reaction and Rydon Smith reaction.

In use of the present substance for the medicines and pharmaceuticals, the conventional methods can be employed for the preparation and administration of such medicines and pharmaceuticals. For instance, they can be administered by injection or oral or rectal application. The preparation forms include injections, powder, granules, tablet, suppository, etc.

Various kinds of adjuvants used for the medicines and pharmaceuticals, namely carriers and other assistants, such as stabilizer, antiseptic, analgesic, emulsifier, etc., can be contained as far as they give no adverse effect to sulphostin in the preparation of medicines and pharmaceuticals. The sulphostin content of the preparations can be varied over a wide range depending on the preparation form and other factors, but generally the preparations contain 0.01 to 100% by weight, preferably 1 to 70% by weight of sulphostin, the remainder containing a carrier and other adjuvants commonly used for the medicines and pharmaceuticals.

The dosage of sulphostin, although variable depending on the condition of the disease and other factors, is about 0.01 to 800 mg per day for adult. Where continuous administration is necessary, it is desirable to restrain the daily dose.

The dipeptidylpeptidase IV inhibitory action of sulphostin is described below with reference to test examples.

TEST EXAMPLE 1
Measurement of Dipeptidyl Peptidase IV Activity

Measurement was made as described below according to the literature (Biochem. Biophys. Acta, 258, 591–599 (1972)). The present substance was added to 0.025 ml of 3.2 mM Glycyl proryl β-naphthylamide (Bachem, Switzerland) and 0.1 ml of 0.1 M tris-maleate buffer (pH 7.2), and then water was added to make the final volume 0.2 ml, thereby preparing a mixed solution. This mixed solution was heated at 37° C. for 10 minutes, and a 0.025 ml of a dipeptidylpeptidase IV solution partially purified by ammonium sulfate fractionation from a homogenate of the rat kidney was added to the above mixed solution and reacted at 37° C. for one hour. To this solution, 0.1 ml of a 0.5 M sodium citrate buffer (pH 3.78) containing 10% of polyoxyethylene sorbitan monolaurate (amount of ethylene oxide added: 20 mol) and 0.2% of first garnet GBC salt (Sigma Inc., USA) was added to stop the reaction, and the absorbance (a) at 525 nm was measured. The absorbance (b) of a blank containing no present substance but the above buffer alone was also measured. The dipeptidyl peptidase IV inhibition rate was calculated from the formula: [(b−a)/b]×100. The dipeptidyl peptidase IV inhibitory activity values of the compound of the present invention determined in various concentrations by the above method are shown in Table 1.

TABLE 1

| Concentration (μg/ml) | Inhibition rate % |
| --- | --- |
| 0.0025 | 23 |
| 0.005 | 42 |
| 0.01 | 54 |
| 0.02 | 67 |
| 0.05 | 82 |

As shown above, sulphostin shows a strong inhibitory action against dipeptidyl peptidase IV, and its $IC_{50}$ value was 0.0082 μg/ml.

Industrial Applicability

The novel physiologically active substance sulphostin according to the present invention can be used for the medicinal and pharmaceutical preparations such as immunoregulator, hormone regulator, anti-HIV drug, anti-allergic drug, antiinflammatory drug, antirheumatic drug, etc.

What is claimed is:
1. A physiologically active substance sulphostin showing the following physicochemical properties:
1) Appearance: white powder;
2) Molecular weight: 272;
3) Molecular formula: $C_5H_{13}N_4O_5SP$;
4) Solubility: soluble in water and insoluble in lower alcohol, acetone, ethyl acetate, hexane and petroleum ether;
5) Rf value measured by silica gel thin-layer chromatography: 0.28 with a developing solvent of n-butanol, acetic acid and water (2:1:1);
6) Ultraviolet absorption spectrum: A terminal absorption is shown;
7) Infrared absorption spectrum: when measured in a potassium bromide tablet, the following specific absorption bands ($cm^{-1}$) are shown: 3510, 3355, 3250, 1672, 1658, 1624, 1545, 1365, 1308, 1240, 1188, 1130, 1064 and 922;
8) Proton NMR spectrum: when measured in heavy water, the following signals δ(ppm) are shown: 4.18 (1H, dd, J=6.8, 12.0 Hz), 3.82 (1H, tdd, J=5.1, 7.3, 13.0 Hz), 3.70 (1H, tdd, J=5.1, 6.7, 13.0 Hz), 2.39–2.44 (1H, m), 2.10–2.28 (1H, m), and 1.89–2.03 (2H, m);
9) Carbon 13 NMR spectrum: when measured in heavy water, the following signals δ(ppm) are shown: 20.5, 24.2, 45.4, 51.3 and 172.4;

10) Phosphorus NMR spectrum: when measured in heavy water, the following signal δ(ppm) is shown: 6.01;
11) Specific rotation: $[\alpha]_D^{28}$ –21.5° (c 0.52, H$_2$O);
12) Melting point: 203–208° C. (decomposed);
13) Color reaction: positive to ninhydrin reaction and Rydon-Smith reaction.

Figure 2:
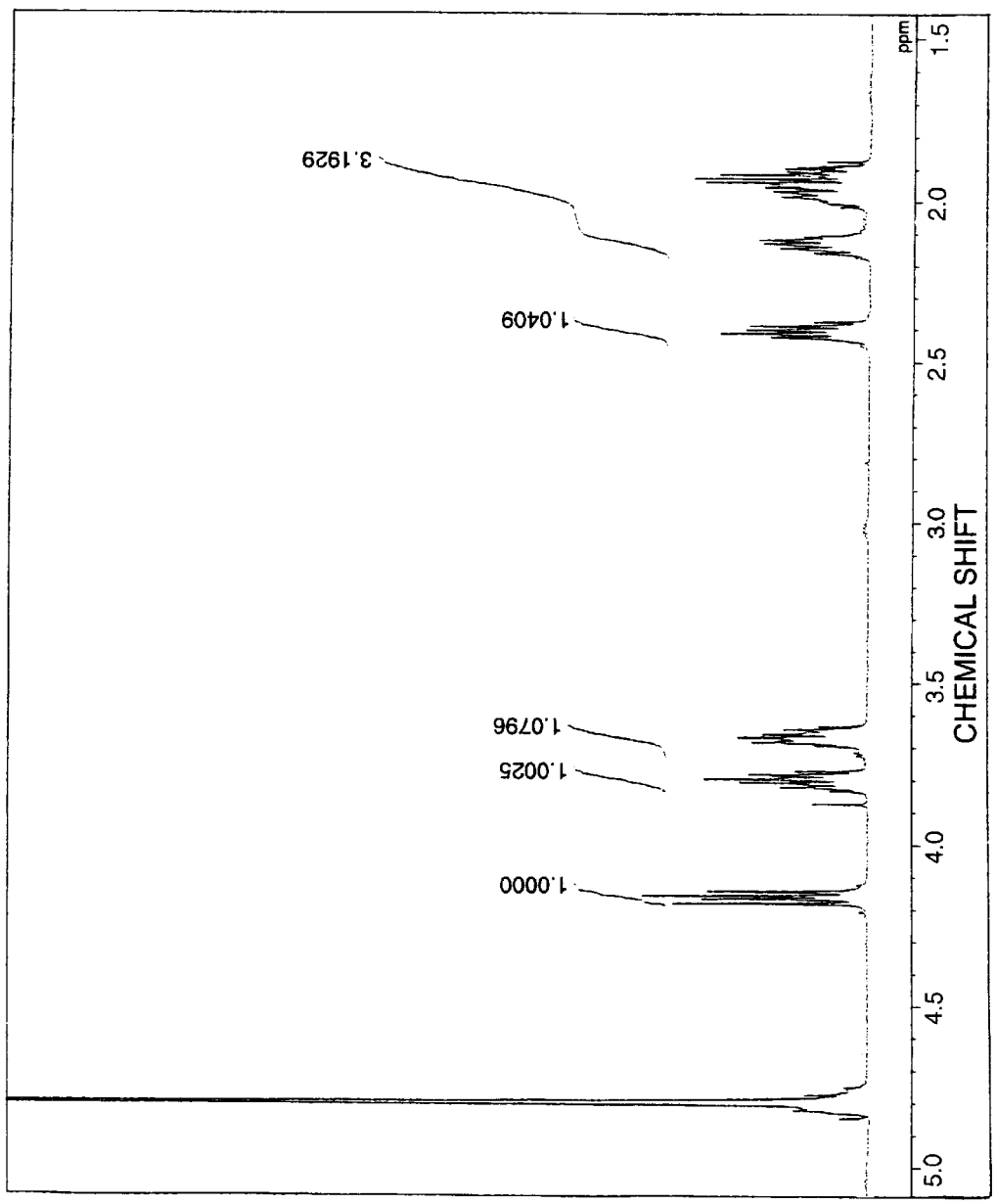
FIG. 2 is a proton NMR spectrum of sulphostin measured in heavy water.
Figure 3:
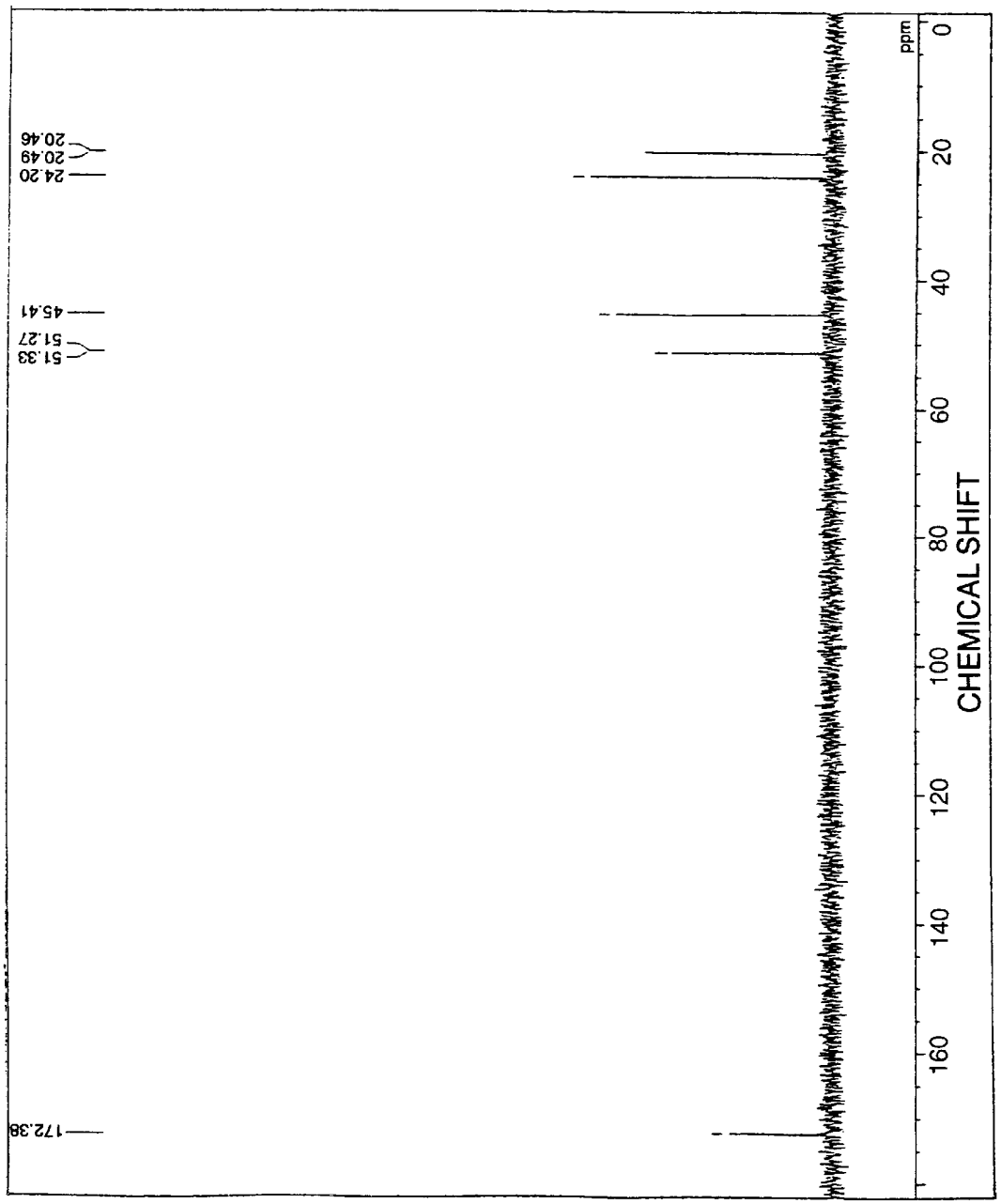
FIG. 3 is a carbon NMR spectrum of sulphostin measured in heavy water.
Figure 4:
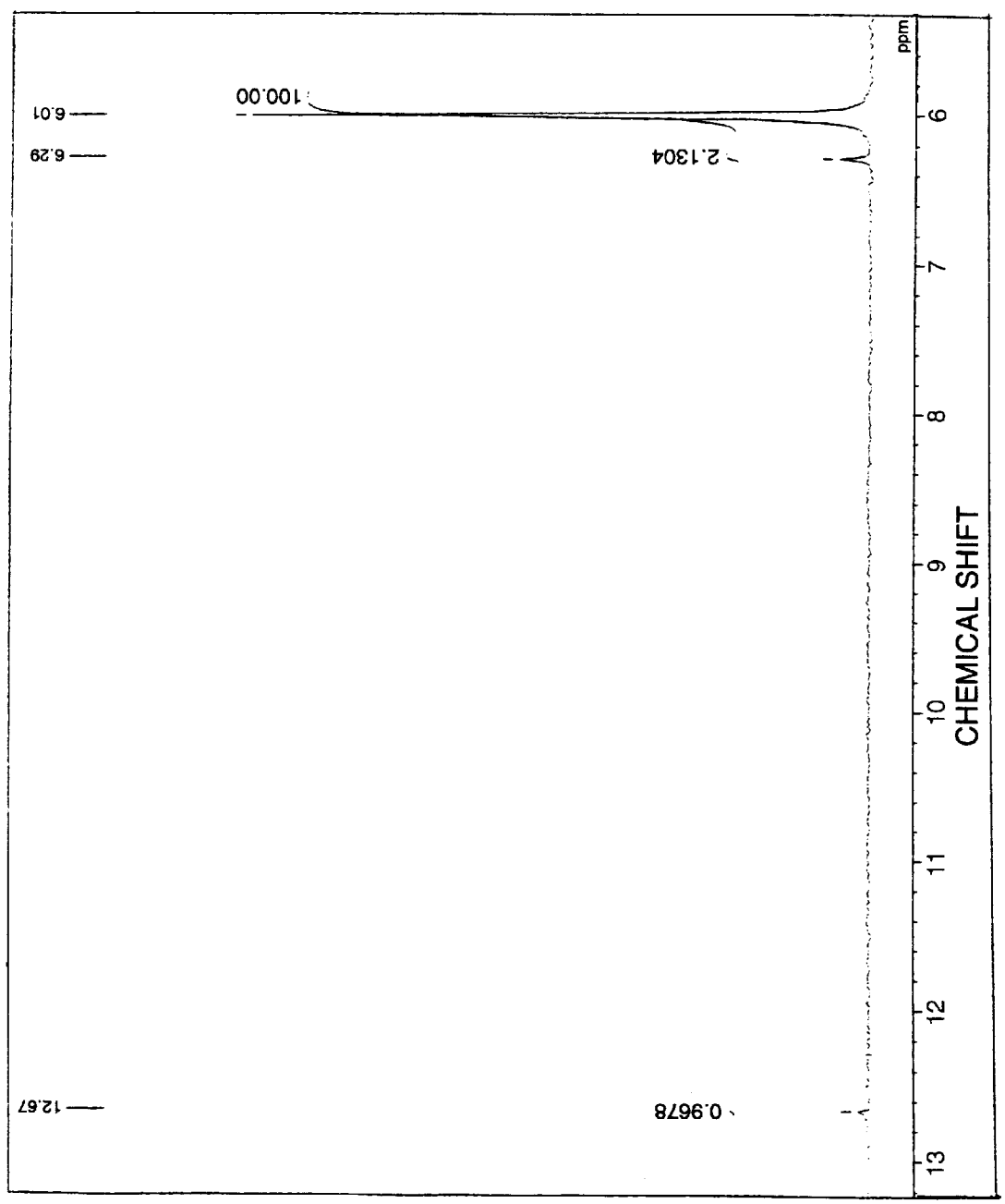
FIG. 4 is a phosphorus NMR spectrum of sulphostin measured in heavy water.

2. A physiologically active substance sulphostin showing the following physicochemical properties:
1) Appearance: whit powder;
2) Molecular weight: 272;
3) Molecular formula: C$_5$H$_{13}$N$_4$O$_5$SP;
4) Solubility: soluble in water and insoluble in lower alcohol, acetone, ethyl acetate, hexane and petroleum ether;
5) Rf value measured by silica gel thin-layer chromatography: 0.28 with a developing solvent of n-butanol, acetic acid and water (2:1:1);
6) Ultraviolet absorption spectrum: A terminal absorption is shown;
7) Infrared absorption spectrum: as shown in FIG. 1 of the attached drawings when measured in a potassium bromide tablet;
8) Proton NMR spectrum: as shown in FIG. 2 of the accompanying attached drawings when measured in heavy water;
9) Carbon 13 NMR spectrum: as shown in FIG. 3 of the attached drawings when measured in heavy water;
10) Phosphorus NMR spectrum: as shown in FIG. 4 of the attached drawings when measured in heavy water;
11) Specific rotation: $[\alpha]_D^{28}$ –21.5° (c 0.52, H$_2$O);
12) Melting point: 203–208° C. (decomposed);
13) Color reaction: positive to ninhydrin reaction and Rydon-Smith reaction.

3. A process for producing the physiologically active substance sulphostin, which comprises culturing a microorganism belonging to the genus Streptomyces and having an ability to produce the physiologically active substance sulphostin set out in claim 1 or 2, producing and accumulating the physiologically active substance sulphostin in the culture, and harvesting the substance from the culture.

4. A dipeptidyl peptidase IV inhibitor comprising the physiologicvally active substance sulphostin set out in claim 1 or 2 as an active ingredient.

5. A drug comprising the physiologically active substance sulphostin set out in claim 1 or 2 as an active ingredient.

6. Streptomyces sp. MK251-43F3 or the mutants thereof having an ability to produce the physiologically active substance sulphostin.

* * * * *